(12) United States Patent
Yu et al.

(10) Patent No.: US 10,982,242 B2
(45) Date of Patent: Apr. 20, 2021

(54) COORDINATED-CONTROL COENZYME Q10 FERMENTATION PRODUCTION PROCESS BASED ON ONLINE OXYGEN CONSUMPTION RATE AND ELECTRICAL CONDUCTIVITY

(71) Applicants: SHANGYU NHU BIOLOGICAL CHEMICAL CO., LTD., Shangyu (CN); ZHEJIANG UNIVERSITY, Hangzhou (CN); ZHEJIANG NHU COMPANY LTD., Shaoxing (CN)

(72) Inventors: Hongwei Yu, Hangzhou (CN); Yong Lv, Shangyu (CN); Yong Li, Shangyu (CN); Jianbo Chen, Shangyu (CN); Shaofeng Chen, Shangyu (CN); Weifeng Li, Shangyu (CN); Hongmei Zhang, Shaoxing (CN); Yongqiang Zhu, Shangyu (CN)

(73) Assignees: SHANGYU NHU BIOLOGICAL CHEMICAL CO., LTD., Shangyu (CN); ZHEJIANG UNIVERSITY, Hangzhou (CN); ZHEJIANG NHU COMPANY LTD., Shaoxing (CN)

( * ) Notice: Subject to any disclaimer, the term of this patent is extended or adjusted under 35 U.S.C. 154(b) by 212 days.

(21) Appl. No.: 15/757,936

(22) PCT Filed: Oct. 21, 2016

(86) PCT No.: PCT/CN2016/102788
§ 371 (c)(1),
(2) Date: Mar. 6, 2018

(87) PCT Pub. No.: WO2017/071529
PCT Pub. Date: May 4, 2017

(65) Prior Publication Data
US 2018/0245113 A1    Aug. 30, 2018

(30) Foreign Application Priority Data
Oct. 26, 2015 (CN) .......................... 201510703113.2

(51) Int. Cl.
C12P 7/66 (2006.01)
C12Q 3/00 (2006.01)
C12N 1/20 (2006.01)
C12R 1/01 (2006.01)

(52) U.S. Cl.
CPC ............... *C12P 7/66* (2013.01); *C12N 1/20* (2013.01); *C12Q 3/00* (2013.01); *C12R 1/01* (2013.01)

(58) Field of Classification Search
CPC .... C12P 7/66; C12N 1/20; C12N 1/00; C12Q 3/00; C12R 1/01
See application file for complete search history.

(56) References Cited

U.S. PATENT DOCUMENTS 6,150,133 A * 11/2000 Mead ............... C12M 41/32
435/69.1

FOREIGN PATENT DOCUMENTS

| CN | 102168115 A | * | 8/2011 |
| CN | 102876743 A | * | 1/2013 |
| CN | 102876743 A | | 1/2013 |
| CN | 103509728 A | | 1/2014 |
| CN | 103509729 A | | 1/2014 |
| CN | 103509816 A | | 1/2014 |

OTHER PUBLICATIONS

Paquet et al., International Dairy Journal, 2000, 10: 391-399. (Year: 2000).*
Ha et al., Controlling the Sucrose Concentration Increases Coenzyme Q10 Production in Fed-Batch Culture of Agrobacterium Tumefaciens, Appl Microbiol Biotechnol., vol. 76, May 2007, abstract.

* cited by examiner

*Primary Examiner* — Allison M Fox
*Assistant Examiner* — Qing Xu
(74) *Attorney, Agent, or Firm* — Jiwen Chen; Jacobson Holman PLLC

(57) ABSTRACT

The present invention relates to an optimized fermentation process of coenzyme Q10, particularly to a fermentation process of coenzyme Q10 via flow feeding based on cooperative control of changes of online oxygen consumption rate and conductivity. During the fermentation process of coenzyme Q10 production strains, the oxygen consumption rate is controlled between 30-150 mmol/L·h and the conductivity is maintained between 3.0-30.0 ms/cm via flow feeding, so as to facilitate strain growth and the start of coenzyme Q10 synthesis and accumulation. The present invention can substantially increase output of coenzyme Q10 and greatly reduce the production cost with simple process control and strong operability, thus being applicable to large-scale industrial production.

6 Claims, 3 Drawing Sheets

COORDINATED-CONTROL COENZYME Q10 FERMENTATION PRODUCTION PROCESS BASED ON ONLINE OXYGEN CONSUMPTION RATE AND ELECTRICAL CONDUCTIVITY

This is a U.S. national stage application of PCT Application No. PCT/CN2016/102788 under 35 U.S.C. 371, filed Oct. 21, 2016 in Chinese, claiming priority of Chinese Application No. 201510703113.2, filed Oct. 26, 2015, all of which are hereby incorporated by reference.

FIELD OF THE INVENTION

The present invention relates to the fermentation field, particularly to an optimized production method of coenzyme Q10 through fermentation of such microorganism as *Rhodobacter sphaeroides* and relevant operation and control techniques, and specifically to a new fermentation production process of coenzyme Q10 based on cooperative control of a metabolism parameter-oxygen consumption rate and a nutrition supply index-conductivity.

BACKGROUND OF THE INVENTION

Coenzyme $Q_{10}$ ($CoQ_{10}$), also known as ubiquinone or ubidecarenone, has a chemical name of 2,3-dimethoxy-5-methyl-6-decyl isopentenyl benzoquinone. As a kind of metabolism activating agent, the bioactivity of coenzyme $Q_{10}$ comes from the redox characteristic of its quinone ring and the physicochemical property of its side chain, thus having such function as oxidation resistance, elimination of free radicals, improvement of immunity of the organism and anti-aging. Clinically, it is extensively applied for the treatment of various heart diseases, cancers, diabetes, acute chronic hepatitis, Parkinsonism and other diseases. In addition, it is also widely used in cosmetics and anti-aging health care products.

Production of coenzyme $Q_{10}$ in microbiological fermentation process is mainly adopted at home and abroad because of its high bioactivity, no limit on raw material and improvement of fermentation production capacity through strain breeding and optimization of fermentation process. However, the biological fermentation process is difficult to be controlled and it is very hard for such control parameters as pH, DO, strain concentration and content in traditional fermentation process to accurately reflect and control the entire fermentation process. Therefore, it is very necessary to introduce more reliable and rapid parameters to reflect the fermentation state, so as to take positive and effective measures to control the entire fermentation process based on these parameters.

Previously reported technical research related to fermentation of coenzyme $Q_{10}$ mainly focuses on the improvement of coenzyme $Q_{10}$ production level through technical innovation of a genetic process, or the investigation of influences on product synthesis through mutagenesis of strain, simple nitrogen source optimization or optimization and adjustment experiment of such single factor as the addition amount of phosphate during process. Some patent literatures also reported the control and optimization of fermentation process through adjusting the glucose feeding rate during process. These researches and technologies only focus on the improvement of output of coenzyme $Q_{10}$ from single factor with certain effects. However, there is absence of fundamental analysis on dynamic physiological process and nutritional requirements of coenzyme $Q_{10}$ production strains, and no appropriate method has been found to study and control the two most important parameters for coenzyme $Q_{10}$ fermentation-oxygen consumption and nutrition supply level to achieve the purpose of improving production capacity.

Previously reported feeding processes are generally in the manner of feed-batch or flow feeding. However, the feeding time and feeding amount are guided by empirical value or offline sampling test of substrate concentration, which may objectively give rise to delayed feeding and excessive or insufficient feeding. Conductivity can be used to represent ion concentration in fermentation system, so as to directly reflect the nutrient consumption of strain in cultivation system, especially the consumption of inorganic ion. Online conductivity electrode can be used to achieve real-time online reflection of the nutrient consumption level of strain so as to guide the feeding time and feeding rate in the feeding process. Previously reported conductivity during fermentation process can only be used to monitor changes of the fermentation process, but is rarely seen in feedback of feeding control.

Coenzyme $Q_{10}$ production strains have different demands on oxygen and nutrition in different stages. Through reasonable control of oxygen and nutrition supply level during the process, the entire fermentation can be controlled from the source and the process can be easily controlled to ensure stable production and reduced production cost.

Patent CN102876743A disclosed an online staged control process based on oxygen consumption rate and the accumulation of coenzyme $Q_{10}$ has been significantly improved.

SUMMARY OF THE INVENTION

The technical problem needed to be solved in the present invention is to provide a new fermentation process of coenzyme $Q_{10}$ based on cooperative control of the oxygen consumption rate OUR and the nutrition supply parameter conductivity. Such process can steadily improve the fermentation production level of coenzyme $Q_{10}$ with data for reference of the entire fermentation process and is thus applicable to large-scale industrial production.

Disclosed is a fermentation production process of coenzyme Q10 based on online cooperative control of oxygen consumption rate and conductivity. During the fermentation process of coenzyme Q10 production strains, the oxygen consumption rate is controlled between 30-150 mmol/L·h and the conductivity is stabilized between 5.0-30.0 ms/cm, so as to facilitate strain growth and the start of coenzyme Q10 synthesis and accumulation.

Through extensive and thorough research, inventors of the present invention discovered that the output of coenzyme Q10 can be substantially improved through online control of the oxygen consumption rate (OUR) by keeping a stable high-level oxygen consumption rate (30-150 mmol/L·h) for the fermentation system and maintaining a steady conductivity (5.0-30.0 ms/cm) via feeding during the fermentation process. Since conductivity is conduction current density in the medium, it can reflect ion concentration in the reaction solution to a certain degree and it can represent the nutrition parameter and environmental index of microorganism in fermentation liquor. Hence, appropriate conductivity can maintain a stable growing environment for microorganism, so as to ensure the growth of microorganism and accumulation of products; OUR refers to the oxygen consumption rate of microorganism and it can accurately represent the oxygen demand of microorganism. The new method based on the joint control of conductivity and OUR can guarantee the offer of sufficient nutrition and oxygen for rapid growth of coenzyme Q10 production strains and the accumulation of products.

It is preferred that the oxygen consumption rate is controlled between 30~90 mmol/L·h during the fermentation process of coenzyme Q10 production strains.

It is preferred that the conductivity of fermentation liquor is controlled between 10-20 ms/cm during the fermentation process of coenzyme Q10 production strains.

In the present invention, the oxygen consumption rate is adjusted via the agitation speed and air flow, and the conductivity is adjusted in the manner of flow feeding or feed-batch.

Wherein, the formula of feed liquor used in flow feeding or feed-batch is as follows:

In 1 L feed liquor, there are 8~12 g yeast powder, 5~10 g ammonium sulfate, 1~2 g magnesium sulfate, 36 g sodium chloride, 2~4 g monopotassium phosphate, 2~4 g dipotassium phosphate, 1~2 g calcium chloride and 0.013~0.025 g biotin with pH value of 7.0 and conductivity of the feeding culture medium of 13.5~23 ms/cm.

Fermentation process in the present invention comprises: inoculation of coenzyme Q10 production strains obtained from seed cultivation into fermentation tank containing fermentation medium, cultivation of coenzyme Q10 production strains under appropriate fermentation conditions, detection of oxygen consumption rate and conductivity of culture medium during cultivation process, and adjustment of fermentation conditions based on detection results.

It is further preferred that the fermentation process comprises the following stages and steps:
(1) During 0~24th hour, controlling the agitation speed at 400 rpm and air flow at 9 L/min when the oxygen consumption rate increases rapidly and keeps at 30-50 mmol/L·h, and the conductivity decreases to 7-16 ms/cm;
(2) During 2436th hour, increasing the agitation speed to 450 rpm and keeping the air flow at 9 L/min when the oxygen consumption rate is 50-60 mmol/L·h;
(3) During 36~60th hour, keeping the agitation speed at 450 rpm and increasing the air flow to 16 L/min when the oxygen consumption rate is 60-70 mmol/L·h;
(4) During 6090th hour, keeping the agitation speed at 450 rpm and increase the air flow to 20 L/min when the oxygen consumption rate is 70-90 mmol/L·h;
(5) During 90100th hour, controlling the agitation speed at 400 rpm when the oxygen consumption rate is 70-90 mmol/L·h;
(6) After 100th hour, controlling the air flow at 16 L/min when the oxygen consumption rate is 50-60 mmol/L h;

Along with the growth of strain in step (2)~(6), substrate in the culture medium is consumed and the conductivity decreases. When the conductivity of the culture medium is equal to or lower than 15 ms/cm, feed-batch of flow feeding is started to keep conductivity of the fermentation liquor between 10-20 ms/cm.
(7) Collecting microbial cells in the fermentation liquor through solid-liquid separation;
(8) Extracting coenzyme Q10 from microbial cells with organic solvent.

During the abovementioned fermentation process, by keeping the oxygen consumption rate at 30-90 mmol/L·h and the conductivity at 10~20 ms/cm based on feedback of cooperative control of feeding via oxygen consumption rate and conductivity, the growth rate of dry cell weight DCW of coenzyme Q10 reaches 0.8-1.0 g/L·h and the synthesis rate of coenzyme Q10 product reaches 50-100 mg/L·h.

In the present invention, the oxygen consumption rate is calculated in the following formula:

$$OUR = \frac{F_{in}}{V}\left[C_{O_2 in} - \frac{C_{inert\ in} \cdot C_{O_2 in}}{1 - (C_{O_2 out} + C_{CO_2 out})}\right] \cdot f$$

$$CER = \frac{F_{in}}{V}\left[\frac{C_{inert\ in} \cdot C_{O_2 out}}{1 - (C_{O_2 out} + C_{CO_2 out})} - C_{O_2 in}\right] \cdot f$$

$$f = \frac{273}{273 + t_{in}} \cdot P_{in} \cdot \frac{1}{1+h} \times 10^{-5}$$

Wherein: $F_{in}$ refers to inlet air flow L/min; V stands for fermentation liquor volume L; $C_{inert\ in}$\$C_{O2in}$\$C_{CO2in}$ respectively refers to the mass fraction of inert gas, oxygen and carbon dioxide in inlet air; $C_{O2out}$\$C_{CO2out}$ respectively stands for the mass fraction of oxygen and carbon dioxide in outlet air; $P_{in}$ refers to the absolute pressure of inlet air Pa; $t_{in}$ refers to the inlet air temperature ° C.; and h refers to the relative humidity of inlet air %.

Fermentation of coenzyme Q10 is an oxygen-consuming and substrate-consuming production and fermentation process, and changes of oxygen supply and nutrition have important impacts on strain growth and synthesis of products. Inventors of the present invention studied three different feeding modes-only flow feeding of glucose and potassium phosphate, flow feeding of glucose and potassium phosphate and feed-batch of culture medium, and flow feeding of glucose, potassium phosphate and culture medium in 10 L, 15 L and 40 L fermentation tank by taking OUR as control variable for staged oxygen supply. Impacts of the three feeding modes on fermentation and experimental results show that the growing status of strain and the synthesis rate of coenzyme Q10 can be accelerated through taking OUR as control variable for staged control of oxygen supply, keeping higher oxygen supply in earlier stage, decreasing oxygen supply by reducing agitation speed or ventilation volume in middle and later stage and maintaining stable conductivity via feeding during fermentation process.

Therefore, inventors of the present invention propose the staged cooperative control strategy of taking OUR as control variable for oxygen supply and conductivity as control variable for nutrition, keeping higher oxygen supply in earlier stage to accelerate rapid growth of strain and quick start of coenzyme Q10 synthesis, decreasing oxygen supply by reducing agitation speed or ventilation volume in middle and later stage to control respiratory metabolism of strain and maintain higher specific production rate and substrate conversion efficiency, and maintaining stable conductivity via feeding in the whole process, so as to maintain a relatively stable production environment for strain and keeping a higher synthesis rate of coenzyme Q10.

During fermentation process, the oxygen consumption rate is calculated for oxygen supply through the agitation speed, ventilation volume or addition of substrate and the detection of oxygen concentration and carbon dioxide concentration in the fermentation tail gas system; and the conductivity is used to guide feeding for nutrition, so as to achieve adjustment of oxygen supply and nutrition level during fermentation process.

Control of Oxygen Consumption Rate and Conductivity

The present invention discloses a control strategy of staged oxygen supply based on the cooperative control of oxygen consumption rate (OUR) which is taken as a control variable and conductivity, and also a new control process for fermentation production of coenzyme Q10 with such microorganism as *Rhodobacter sphaeroides*. Experiments in the present invention indicate that a higher specific production rate and substrate conversion efficiency can be maintained through keeping higher oxygen supply in earlier stage, limiting oxygen supply in later stage and maintaining a stable conductivity by feeding during the fermentation process, so as to greatly improve the productivity of coenzyme Q10, improve the utilization ratio of substrate, reduce raw material consumption and lower the cost.

Production Strains

There is no special restriction on strains representing coenzyme Q10 and applicable to method in the present invention. They can be existing production strains for production of coenzyme Q10 or engineering strains reconstructed in conventional method or genetic engineering approach. Representative production strains are preferred to be *Rhodobacter sphaeroides* with preservation number of CGMCC No. 5997, CGMCC No. 5998 or CGMCC No. 5999.

The abovementioned CGMCC No. 5997, CGMCC No. 5998 or CGMCC No. 5999 strains are kept by China General Microbiological Culture Collection Center (address: Institute of Microbiology, Chinese Academy of Sciences, Building 3, No. 1 West Beichen Road, Chaoyang District, Beijing; date of preservation: Apr. 13, 2012).

Patents CN103509718 A, CN103509816A and CN103509729A disclosed a reconstruction method of strain in genetic engineering approach. With such method, production strains for synthesis of coenzyme Q10 can be obtained and cultured under conventional appropriate conditions for synthesis of coenzyme Q10. In the present invention, it is found that a higher synthetic amount of coenzyme Q10 can be obtained from reconstructed strains in genetic approach through optimizing process conditions.

Culture Medium

There is no special restriction on the culture medium formula in seeding flask used in method in the present invention and various conventional culture mediums can be used. In 1 L culture medium, there are 1 g yeast powder, 1 g ammonium chloride, 1 g sodium chloride, 0.0028 g ferric citrate, 0.6 g monopotassium phosphate, 0.9 g dipotassium phosphate, 0.25 g magnesium sulfate and 0.1 g calcium chloride with pH value of 7.0.

With respect to the culture medium formula in seeding tank in the summary of invention above, in 1 L culture medium, there are 1 g yeast powder, 1 g ammonium chloride, 1 g sodium chloride, 0.0028 g ferric citrate, 0.6 g monopotassium phosphate, 0.9 g dipotassium phosphate, 0.25 g magnesium sulfate and 0.1 g calcium chloride with pH value of 7.0.

With respect to the culture medium formula in fermentation tank in the summary of invention above, in 1 L culture medium, there are 8 g yeast powder, 3 g ammonium chloride, 2.8 g sodium chloride, 0.005 g ferric citrate, 0.6 g monopotassium phosphate, 0.9 g dipotassium phosphate, 12.55 g magnesium sulfate and 0.1 g calcium chloride with pH value of 7.0.

To ensure the fermentation process, conductivity of the fermentation liquor system is stabilized within an appropriate range and formula of the feeding culture medium is: in 1 L feeding liquor, there are 8~12 g yeast powder, 5~10 g ammonium sulfate, 1~2 g magnesium sulfate, 3~6 g sodium chloride, 2~4 g monopotassium phosphate, 2~4 g dipotassium phosphate, 1~2 g calcium chloride and 0.013~0.025 g biotin with pH value of 7.0 and conductivity of the feeding culture medium of 13.5~23 ms/cm.

Volume of the fermentation tank in the summary of invention above can be 10 L~200 m$^3$ and it is preferred to be 15 L~150 m$^3$.

Advantages of the present invention lie in:

(1) Comprehensive and accurate detection and analysis of the fermentation process of coenzyme Q10, digital control of the important growth control parameters-OUR and conductivity during process, simple process control, strong operability and significantly improved production efficiency.

(2) The present invention can effectively improve the output of coenzyme Q10, lower the production cost with simple operation, be environment friendly and be beneficial to further industrial amplification, popularization and application.

DESCRIPTION OF THE PREFERRED EMBODIMENT

Figure 1:
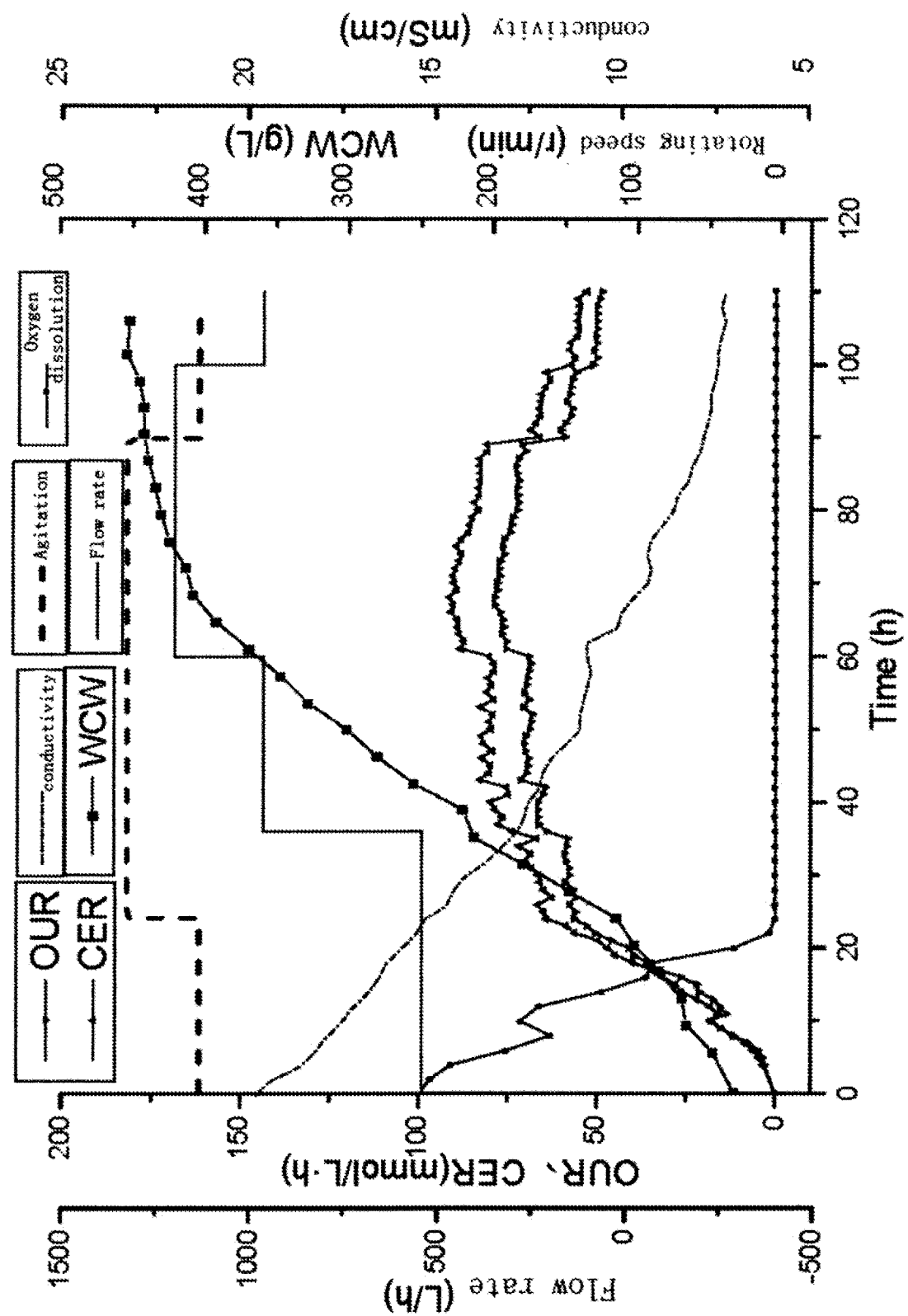
FIG. 1 shows changes of OUR, CER, DO, conductivity, strain concentration, agitation speed and air flow along with the time during the fermentation process of coenzyme Q10 in existing technology.

Next, the present invention will be further described with embodiments. It should be understood that these embodiments are only used to illustrate the present invention instead of limiting the protection scope of the present invention. If specific conditions in experiment methods are not indicated in embodiments below, general conditions can be followed usually. Unless otherwise specified, all percentages and shares shall be calculated based on weight.

Instruments in the present invention: 10 L fermentation tank: manufactured by Shanghai BaoXing Bio-Engineering Equipment Co., Ltd.; 15 L fermentation tank: Shanghai Guoqiang Biochemical Equipment Co., Ltd.; tail gas mass spectrometer: MAX300-LG from Extrel; and online conductivity measuring instrument: Mettler-Toledo.

Coenzyme Q10 production strains used in embodiments in the present invention are *Rhodobacter sphaeroides*.

Embodiment 1 Continuous Flow Feeding Process (1) Seed culture: cultured slope was washed with sterile water, bacterium suspension containing $10^8$~$10^9$ cells per milliliter was prepared, 10 ml of suspension was moved into a seeding flask with loading capacity of 500 ml/1000 ml and cultivated for 22-26 hours at 30° C. under 180~250 rpm to obtain seed liquor.

(2) Fermentation cultivation: seed liquor from step (1) was inoculated into 10 L fermentation tank in the amount of 10%, the culture temperature was kept at 29-33° C. and in-tank pressure at 0.03~0.05 Mpa, staged control strategy was taken for oxygen supply, the initial agitation speed was maintained at 500 rpm and air flow at 6 L/min after inoculation when OUR rapidly increases to 30-50 mmol/L·h and agitation speed increases to 500-700 rpm in 24 hours along with the end of growth delay period and the start of rapid logarithmic growth phase of strain, residual glucose was controlled in tank between 0.5-2.0% and cultivate for around 110 hours. Process parameters were adjusted and continuous feeding of glucose was stared based on strain growth conditions, process parameters based on changes of the oxygen consumption rate was adjusted and flow feeding of culture medium was started based on changes of the conductivity at the same time.

Oxygen supply control during fermentation process: during fermentation production process of coenzyme Q10 with *Rhodobacter sphaeroides*, high oxygen supply can effectively accelerate strain growth, while limited oxygen can give rise to deformation of mycelial morphology and quick start of synthesis of coenzyme Q10. Hence, staged oxygen supply was adopted for adjustment during fermentation production of coenzyme Q10 with *Rhodobacter sphaeroides*. After start of fermentation in 10 L fermentation tank, along with the increase of strain, OUR and CER slowly increased, indicating the gradual increase of oxygen consumption of strain. After oxygen dissolution for about 20 h, it decreased to around 1-5% and the growth of OUR and CER became stable. However, strains were still in exponential growth phase and strain quantity was still growing, indicating that the respiration intensity of strains was maximal and oxygen supply became a restrictive factor. Oxygen supply was increased by stages to accelerate strain growth and oxygen supply was decreased in later period to promote synthesis of coenzyme Q10 and reduce consumption of substrate. During 0~24th hour, control the agitation speed at 500 rpm and air flow at 6 L/min and OUR slowly became stable to reach 30~50 mmol/L·h along with strain growth when strains were still in exponential growth phase and oxygen supply became a restrictive condition. Through increasing the agitation speed and ventilation volume, oxygen supply level was improved and OUR was kept at 50~60 mmol/L·h during 24~36th hour and 60~70 mmol/L·h during 36~60th hour to promote strain growth. After $60^{th}$ hour, such stage gradually becomes stable and strain quantity no longer increased when coenzyme Q10 rapidly synthesized and accumulated and a higher specific production rate of coenzyme Q10 was maintained by gradually reducing oxygen supply. Then, OUR was maintained between 70~90 mmol/L·h during 60~90th hour, 60~80 mmol/L·h during 90~100th hour and 50~60 mmol/L·h after 100th hour.

Figure 2A:
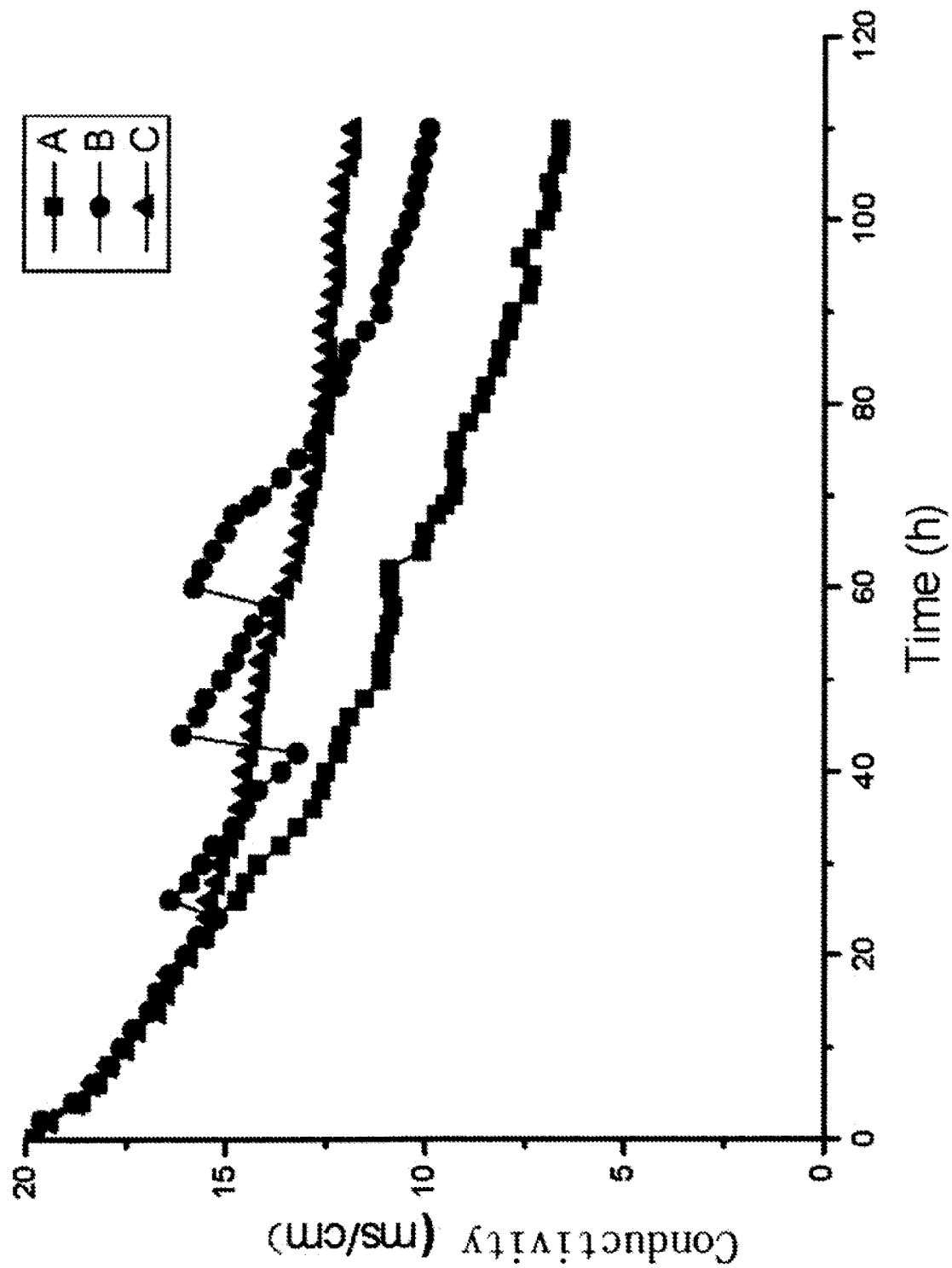
FIG. 2a shows the variation curve of conductivity along with the time in three different feeding modes in embodiment 1 (continuous feeding, curve C), embodiment 3 (intermittent feed-batch, curve B) and embodiment 4 (only feeding glucose and potassium phosphate normally, curve A)

Feeding process control during fermentation process: during fermentation process of coenzyme Q10 with *Rhodobacter sphaeroides*, nutrition medium concentration of the substrate also affected the growth of strain and accumulation of products. During fermentation process, along with the consumption of nutrition substrate in culture medium, the conductivity declines and the growing environment of strain changed, thus resulting in growth and metabolism of strain. During normal fermentation process, only flow feeding of glucose and potassium phosphate was conducted. In this feeding process, in addition to feeding of glucose and monopotassium phosphate based on residual glucose and phospate solubilization in normal process, flow feeding of culture medium was also started along with the multiplication of strain, the consumption of nutrition substrate in fermentation liquor and the gradual decline of conductivity to 15.0 ms/cm. Formula of the feeding culture medium was: in 1 L feed liquor, there were 8~12 g yeast powder, 5~10 g ammonium sulfate, 1~2 g magnesium sulfate, 3~6 g sodium chloride, 2~4 g monopotassium phosphate, 2~4 g dipotassium phosphate, 1~2 g calcium chloride and 0.013~0.025 g biotin with pH value of 7.0 and conductivity of the feeding culture medium of 13.5~23 ms/cm. By controlling the feed rate of culture medium, the conductivity was maintained between 10~20 ms/cm. In FIG. 2a, curve C represented the variation tendency of conductivity in such feeding process and the residual glucose was maintained at 0.5~2.0% in the whole process. After 110th hour, the fermentation ends and the titer arrived at 3350 mg/L.

Embodiment 2 Continuous Flow Feeding Process (1) Seed culture: cultured slope was washed with sterile water, bacterium suspension containing $10^8$~$10^9$ cells per milliliter was prepared, 10 ml of the suspension was moved into seeding flask with loading capacity of 500 ml/1000 ml and cultivated for 22-26 hours at 30° C. under 180-250 rpm.

(2) Fermentation cultivation: seed liquor from step (1) was inoculated into 15 L fermentation tank in the amount of 10%, the culture temperature was kept at 29-33° C. and in-tank pressure at 0.03~0.05 Mpa, staged control strategy was taken for oxygen supply, the initial agitation speed was maintained at 500 rpm and air flow at 9 L/min after inoculation when OUR rapidly increased to 30-50 mmol/L·h and agitation speed increased to 500-700 rpm in 24 hours along with the end of growth delay period and the start of rapid logarithmic growth phase, residual glucose in tank was controlled between 0.5-2.0% and cultivated for around 110 hours. Process parameters was adjusted and continuous feeding of glucose was started based on strain growth conditions, process parameters were adjusted based on changes of the oxygen consumption rate and flow feeding of culture medium was started based on changes of the conductivity at the same time.

Oxygen supply control during fermentation process: staged oxygen supply was adopted for adjustment. Oxygen supply was increased by stages to accelerate strain growth and oxygen supply was decreased in later period to promote synthesis of coenzyme Q10 and reduce consumption of substrate. During 0~24th hour, the agitation speed was controlled at 500 rpm and air flow was controlled at 9 L/min and OUR slowly became stable to reach 30~50 mmol/L·h along with strain growth when strains were still in exponential growth phase and oxygen supply became a restrictive condition. Through increasing the agitation speed and ventilation volume, oxygen supply level was improved and OUR was kept at 50~60 mmol/L·h during 24~36th hour and 60~70 mmol/L·h during 36~60th hour to promote strain growth. After 60th hour, such stage gradually becomes stable and strain quantity no longer increases when coenzyme Q10 rapidly synthesizes and accumulates and a higher specific production rate of coenzyme Q10 is maintained by gradually reducing oxygen supply. Then, OUR is maintained between 70~90 mmol/L·h during 60~90 h, 60~80 mmol/L·h during 90~100th hour and 50~60 mmol/L h after 100th hour.

Feeding process control during fermentation process: in this feeding process, in addition to feeding of glucose and monopotassium phosphate based on residual glucose and phosphate solubilization in normal process, flow feeding of culture medium was also started along with the multiplication of strains, the consumption of nutrition substrate in fermentation liquor and the gradual decline of conductivity to 15.0 ms/cm. Formula of the feeding culture medium was: in 1 L feed liquor, there were 8~12 g yeast powder, 5~10 g ammonium sulfate, 1~2 g magnesium sulfate, 3~6 g sodium chloride, 2~4 g monopotassium phosphate, 2~4 g dipotassium phosphate, 1~2 g calcium chloride and 0.013~0.025 g biotin with pH value of 7.0 and conductivity of the feeding culture medium of 13.5~23 ms/cm. By controlling the feed rate of culture medium, the conductivity was maintained between 10-20 ms/cm and the residual glucose was maintained at 0.5~2.0% in the whole process. After 110th hour, the fermentation ends and the titer arrived at 3420 mg/L.

Embodiment 3 Feed-Batch Process (1) Seed culture: cultured slope was washed with sterile water, bacterium suspension containing $10^8$~$10^9$ cells per milliliter was prepared, 10 ml of suspension was moved into seeding flask with loading capacity of 500 ml/1000 ml and cultivate for 22-26 hours at 30° C. under 180-250 rpm.

(2) Fermentation cultivation: seed liquor from step (1) was inoculated into 10 L fermentation tank in the amount of 10%, the culture temperature was kept at 29-33° C. and in-tank pressure was kept at 0.03~0.05 Mpa, staged control strategy was taken for oxygen supply, the initial agitation speed was maintained at 500 rpm and air flow was maintained at 6 L/min after inoculation when OUR rapidly increased to 30-50 mmol/L·h and agitation speed increased to 500-700 rpm in 24 hours along with the end of growth delay period and the start of rapid logarithmic growth phase, residual glucose in tank was controlled between 0.5-2.0% and cultivate for around 110 h. Process parameters was adjusted and continuous feeding of glucose was started based on strain growth conditions, process parameters was adjusted based on changes of the oxygen consumption rate and flow feeding of culture medium was started based on changes of the conductivity at the same time.

Oxygen supply control during fermentation process: staged oxygen supply is adopted for adjustment. Oxygen supply is increased by stages to accelerate strain growth and oxygen supply is decreased in later period to promote synthesis of coenzyme Q10 and reduce consumption of substrate. During 0~24th hour, the agitation speed was controlled at 500 rpm and air flow at 9 L/min and OUR slowly became stable to reach 30~50 mmol/L·h along with strain growth when strains were still in exponential growth phase and oxygen supply became a restrictive condition. Through increasing the agitation speed and ventilation volume, oxygen supply level was improved and OUR was kept at 50~60 mmol/L·h during 24~36th hour and 60~70 mmol/L·h during 36~60th hour to promote strain growth. After 60th hour, such stage gradually became stable and strain quantity no longer increased when coenzyme Q10 rapidly synthesized and accumulated and a higher specific production rate of coenzyme Q10 was maintained by gradually reducing oxygen supply. Then, OUR was maintained between 70~90 mmol/L·h during 60~90th hour, 60~80 mmol/L·h during 90~100th hour and 50~60 mmol/L·h after 100th hour.

Feeding process control during fermentation process: intermittent feed-batch was adopted and feeding culture medium accounting for 20% of volume of the fermentation liquor was fed at 20th hour, 40th hour and 60th hour respectively during fermentation process. Formula of the feeding culture medium was: in 1 L feed liquor, there were 8~12 g yeast powder, 5~10 g ammonium sulfate, 1~2 g magnesium sulfate, 3~6 g sodium chloride, 2~4 g monopotassium phosphate, 2~4 g dipotassium phosphate, 1~2 g calcium chloride and 0.013~0.025 g biotin with pH value of 7.0. Along with the growth of strain, the culture medium was consumed and the conductivity gradually declined. After each feeding, the conductivity substantially increased and then gradually declined. In FIG. 2a, curve B represented the variation tendency of conductivity during fermentation process in such feeding mode. The residual glucose was maintained at 0.5~2.0% in the whole process. After 110th hour, the fermentation ends and the titer arrived at 3013 mg/L.

Embodiment 4 Control Embodiment (1) Seed culture: cultured slope was washed with sterile water, bacterium suspension containing $10^8$~$10^9$ cells per milliliter was prepared, move 10 ml into seeding flask with loading capacity of 500 ml/1000 ml and cultivate for 22-26 hours at 30° C. under 180-250 rpm.

(2) Fermentation cultivation: seed liquor from step (1) was inoculated into 10 L fermentation tank in the amount of 10%, the culture temperature was kept at 29-33° C. and in-tank pressure was kept at 0.03~0.05 Mpa, staged control strategy was taken for oxygen supply, the initial agitation speed was maintained at 500 rpm and air flow was maintained at 6 L/min after inoculation when OUR rapidly increased to 30-50 mmol/L·h and agitation speed increased to 500-700 rpm in 24 hours along with the end of growth delay period and the start of rapid logarithmic growth phase, residual glucose in tank was controlled between 0.5-2.0% and cultivated for around 110 hours. Process parameters was adjusted and continuous feeding of glucose was started based on strain growth conditions, process parameters were adjusted based on changes of the oxygen consumption rate and flow feeding of culture medium was started based on changes of the conductivity at the same time.

Oxygen supply control during fermentation process: staged oxygen supply was adopted for adjustment. Oxygen supply was increased by stages to accelerate strain growth and oxygen supply was decreased in later period to promote synthesis of coenzyme Q10 and reduce consumption of substrate. During 0~24th hour, the agitation speed was controlled at 500 rpm and air flow was controlled at 9 L/min and OUR slowly became stable to reach 30~50 mmol/L·h along with strain growth when strains were still in exponential growth phase and oxygen supply became a restrictive condition. Through increasing the agitation speed and ventilation volume, oxygen supply level was improved and OUR was kept at 50~60 mmol/L·h during 24~36th hour and 60~70 mmol/L·h during 36~60th hour to promote strain growth. After 60th hour, such stage gradually became stable and strain quantity no longer increased when coenzyme Q10 rapidly synthesized and accumulated and a higher specific production rate of coenzyme Q10 was maintained by gradually reducing oxygen supply. Then, OUR was maintained between 70~90 mmol/L·h during 60~90th hour, 60~80 mmol/L·h during 90~100th hour and 50~60 mmol/L·h after 100th hour.

Feeding process control during fermentation process: taking existing culture process as control embodiment, glucose and potassium phosphate were fed based on residual glucose content and phosphate solubilization concentration during fermentation process. During process engineering of this control embodiment, along with the growth of strain, the substrate was consumed and the conductivity gradually declines. In FIG. 2a, curve A represented the variation tendency of conductivity during feeding process in this control embodiment. The residual glucose was maintained at 0.5~2.0% in the whole process. After 110 hours, the fermentation ends and the titer arrived at 2843 mg/L.

In existing feed-batch process of coenzyme Q10, staged control of oxygen supply was adopted to improve strain growth and coenzyme Q10 accumulation. FIG. 1 showed the variation of OUR, CER and conductivity corresponding to adjustment of agitation speed and air flow during fermentation process. In earlier stage, along with the growth of strain, OUR and CER slowly increased, indicating the gradual increase of oxygen consumption by strain; at around 26th hour, increase of OUR and CER became stable; along with the substrate consumption by strain and dilution caused by feeding, the conductivity continuously declined, but strains were still in exponential growth phase and strain quantity was still growing, indicating that the respiration intensity of strains was maximal and oxygen supply became a restrictive factor. Meanwhile, the decline of conductivity also meant the consumption of nutrient concentration and it might easily result in nutritional imbalance for production environment of strain.

Figure 2B:
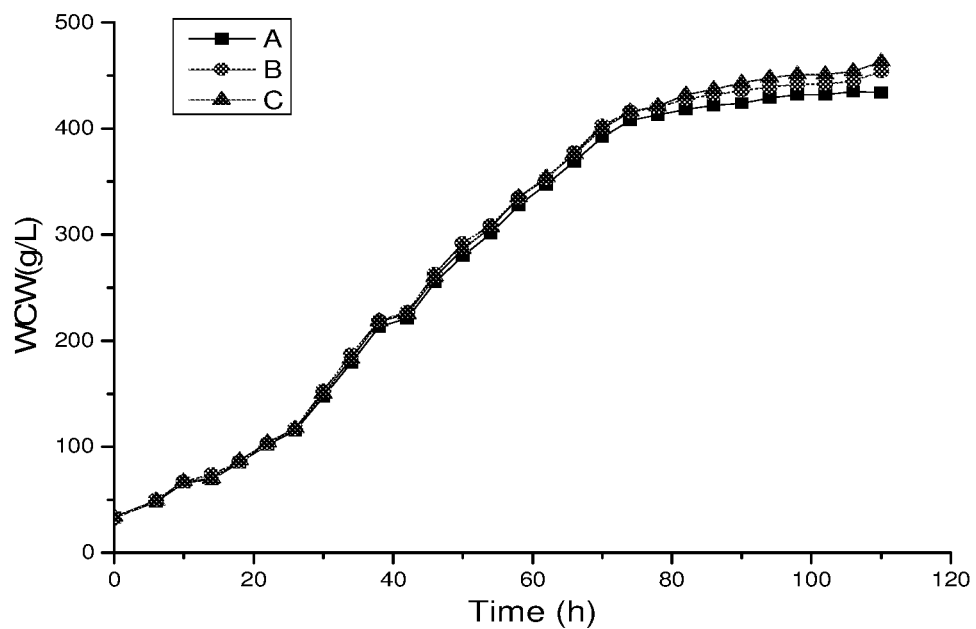
FIG. 2b shows the variation curve of strain concentration along with the time in three different feeding modes in embodiment 1 (continuous feeding, curve C), embodiment 3 (intermittent feed-batch, curve B) and embodiment 4 (only feeding glucose and potassium phosphate normally, curve A)
Figure 2C:
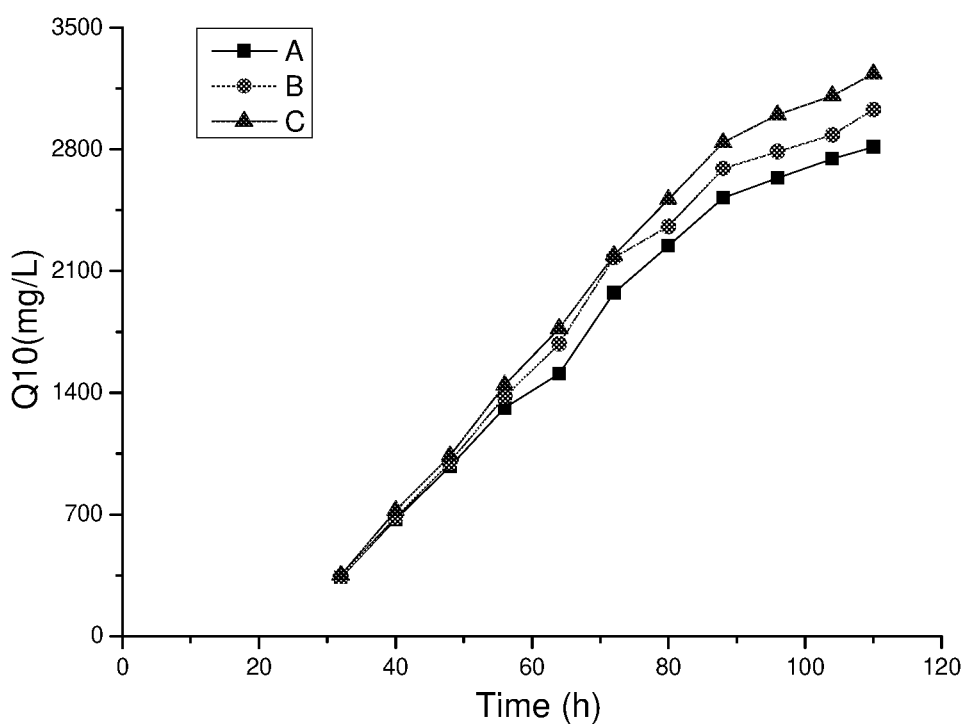
FIG. 2c shows the variation curve of coenzyme Q10 concentration along with the time in three different feeding modes in embodiment 1 (continuous feeding, curve C), embodiment 3 (intermittent feed-batch, curve B) and embodiment 4 (only feeding glucose and potassium phosphate normally, curve A).

In staged oxygen supply control process in 10 L and 15 L experiment tank, inventors of the present invention studied different feeding strategies to reflect the impacts of culture medium feeding based on substrate concentration on fermentation of coenzyme Q10 with online conductivity. FIG. 2a~2c showed variations of conductivity, strain concentration and coenzyme Q10 concentration with different feeding strategies during fermentation of coenzyme Q10.

During fermentation, the conductivity declined along with the growth of strain, the consumption of substrate and the dilution of substrate concentration caused by feeding. From FIG. 2a, it can be seen that the substrate concentration can be stabilized through feed-batch and flow feeding.

From FIG. 2b, it can be seen that the impact of culture medium feeding during process on strain concentration was not obvious during fermentation process. Especially during the earlier stage and later stage of fermentation, with different feeding modes, the strain concentration was slightly improved in the later stage, indicating that the feeding of culture medium during process was beneficial to fermentation status in the later stage.

From FIG. 2c, it can be seen that the start of flow feeding of culture medium after the conductivity declined to 15 ms/cm and the maintenance of relatively stable substrate concentration can obviously improve the accumulation of coenzyme Q10 in the middle and later period of fermentation.

As stated above, during the fermentation process of coenzyme Q10, the strategy of staged oxygen supply and flow feeding shall be adopted to adjust the fermentation process. Therefore, high oxygen supply shall be adopted in the growth stage and earlier synthesis stage of fermentation to promote the rapid growth of strain and quick start of coenzyme Q10; when strain entered into the rapid consumption stage, flow feeding of culture medium shall be started to feed necessary nutrition medium and maintain a reasonable growing environment for strain growth; after strain enters into a stable period, oxygen supply shall be decreased by stages to maintain a higher specific production rate of coenzyme Q10 and reduce the consumption of the substrate glucose. To sum up, such staged oxygen supply and feeding mode will certainly achieve the best physiological property state for production strains and reduce the production cost of coenzyme Q10.

The invention claimed is:

1. A fermentation process for producing coenzyme Q10 by coordinated-control of an oxygen-consumption rate and electrical conductivity of a fermentation culture, comprising the steps of:
   (i) providing a culture medium and coenzyme Q10-production microorganisms in a fermentation tank to obtain the fermentation culture;
   (ii) controlling the oxygen-consumption rate of the fermentation culture at a level between 30-90 mmol/L-h during the fermentation process; and
   (iii) controlling the conductivity of the fermentation culture at a level between 5.0-30.0 ms/cm during the fermentation process, so as to facilitate growth of the microorganisms and initiation of coenzyme Q10 synthesis and accumulation;
   wherein the controlling of the oxygen-consumption rate is conducted online;
   wherein the fermentation process further comprises: inoculation of the microorganisms obtained from seed cultivation into the fermentation tank containing the fermentation culture, cultivation of the microorganisms under appropriate fermentation conditions, detection of the oxygen consumption rate and conductivity of the fermentation culture during the cultivation, and adjustment of fermentation conditions based on detection results;
   wherein the oxygen consumption rate is adjusted via an agitation speed of the fermentation culture and air flow, and the fermentation process comprises the following stages and steps:
   (1) during 0-24th hour, controlling the agitation speed of the fermentation culture at 400 rpm and air flow at 9 L/min, wherein the oxygen consumption rate increases rapidly and keeps at 30-50 mmol/L-h, and the conductivity decreases to 7-16 ms/cm;
   (2) during 24-36th hour, increasing the agitation speed to 450 rpm and keeping the air flow at 9 L/min, wherein the oxygen consumption rate is 50-60 mmol/L-h;
   (3) during 36-60th hour, keeping the agitation speed at 450 rpm and increasing the air flow to 16 L/min, wherein the oxygen consumption rate is 60-70 mmol/L-h;
   (4) during 60-90th hour, keeping the agitation speed at 450 rpm and increasing the air flow to 20 L/min, wherein the oxygen consumption rate is 70-90 mmol/L-h;
   (5) during 90-100th hour, controlling the agitation speed at 400 rpm, wherein the oxygen consumption rate is 70-90 mmol/L-h;
   (6) after 100th hour, controlling the air flow at 16 L/min, wherein the oxygen consumption rate is 50-60 mmol/L-h;
   keeping the conductivity of the fermentation culture between 10-20 ms/cm in stages (2)-(6);
   (iv) collecting microbial cells in the fermentation culture through solid-liquid separation;
   (v) extracting coenzyme Q10 from the microbial cells with an organic solvent; and wherein the coenzyme Q10-production microorganisms are *Rhodobacter sphaeroides*.

2. The fermentation process for producing coenzyme Q10 according to claim 1, characterized in that the conductivity is adjusted in the manner of flow feeding or batch-feeding of a feeding culture medium.

3. The fermentation process for producing coenzyme Q10 according to claim 2, characterized in that a formula of the feeding culture medium used in the flow feeding or batch-feeding is as follows: in 1 L feeding culture medium, there are 8-12 g of yeast powder, 5-10 g of ammonium sulfate, 1-2 g of magnesium sulfate, 3-6 g of sodium chloride, 2-4 g of monopotassium phosphate, 2-4 g of dipotassium phosphate, 1-2 g of calcium chloride and 0.013-0.025 g of biotin with pH value of 7.0; and the conductivity of the feeding culture medium is 13.5-23 ms/cm.

4. The fermentation process for producing coenzyme Q10 according to claim 1, characterized in that the coenzyme Q10-production microorganisms are *Rhodobacter sphaeroides* strains selected from the group consisting of strains from natural selection, strains selected via physical or chemical mutagenesis, and high-producing strains reconstructed with genetic engineering approach.

5. The fermentation process for producing coenzyme Q10 according to claim 1, characterized in that the coenzyme Q10-production microorganisms are *Rhodobacter sphaeroides* strain CGMCC No. 5997, or *Rhodobacter sphaeroides* strain CGMCC No. 5998, or *Rhodobacter sphaeroides* strain CGMCC No. 5999.

6. The fermentation process for producing coenzyme Q10 according to claim 1, characterized in that a volume of the fermentation tank is 10 L-150 $m^3$.

* * * * *